United States Patent [19]

Cirera et al.

[11] Patent Number: 5,112,826
[45] Date of Patent: May 12, 1992

[54] VASODILATORY DIHYDRODIBENZOCYCLOHEPTYLIDEN-ETHYLPIPERAZINE DERIVATIVES

[76] Inventors: Xavier D. Cirera, 271 Avenida Argentina; Romeo R. Andreoli, 6 Calle Roca i Batlle; Pedro P. Lloveras, 94 Calle Viverett; Leonida Bruseghini, 5 Calle Caponata; Jose P. Irurre, 184 Calle Mayor de Sarria, all of Barcelona, Spain

[21] Appl. No.: 336,881

[22] Filed: Apr. 12, 1989

[30] Foreign Application Priority Data

Aug. 2, 1983 [ES] Spain ..................................... 524680

[51] Int. Cl.⁵ .................... A61K 31/495; C07D 295/00
[52] U.S. Cl. ..................................... 514/255; 544/380
[58] Field of Search ........................ 544/380; 514/255

[56] References Cited

U.S. PATENT DOCUMENTS 4,994,463  2/1991  Oshima et al. ....................... 544/380

FOREIGN PATENT DOCUMENTS 357956  3/1970  European Pat. Off. ............. 544/380

*Primary Examiner*—Cecilia Shen
*Attorney, Agent, or Firm*—Michael J. Striker

[57] ABSTRACT

The dihydrodibenzocycloheptyliden-ethylpiperazine derivative has the formula:

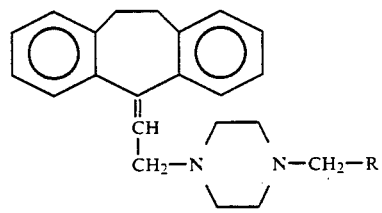

wherein R represents a substituent selected from the group consisting of —CH=CH$_2$; —CO$_2$C$_2$H$_5$; —CH=CH—CO$_2$CH$_3$;

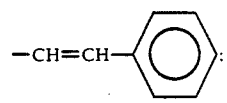

and

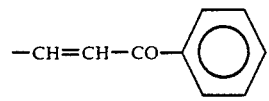

5 Claims, No Drawings

VASODILATORY DIHYDRODIBENZOCYCLOHEPTYLIDEN-ETHYLPIPERAZINE DERIVATIVES

BACKGROUND OF THE INVENTION

The present invention relates to new derivatives of dihydrodibenzocycloheptyliden-ethylpiperazine and is a divisional application based on the earlier copending application Ser. No. 07/054,408 U.S. Pat. No. 4,835,156 has issued in application Ser. No. 07/154,408.

Other agents known which display vasodilatory effects, for example, cinarizine and flunarizine. The derivatives of dihydrodibenzocycloheptylidenethylpiperazine of this invention have not previously been synthesized and investigated for pharmocological activity.

SUMMARY OF THE INVENTION

Accordingly, it is an object of my invention to provide new vasodilatory derivatives of dihydrodibenzocycloheptyliden-ethylpiperazine.

This object is attained according to the present invention by the novel compounds derived from dihydrodibenzocycloheptyliden-ethylpiperazine of the general formula (I)-B:

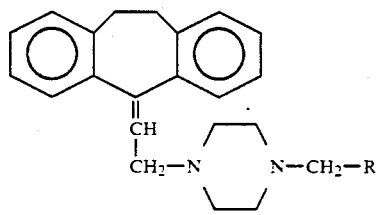

I-B wherein R = —CH=CH$_2$; —CH$_2$OH; —CO$_2$H; —CO$_2$C$_2$H$_5$; —CH=CH—CO$_2$CH$_3$

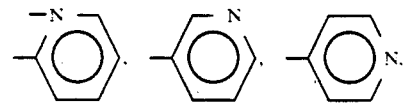

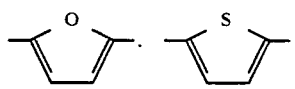

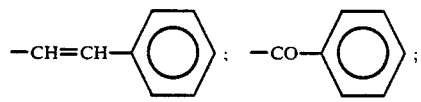

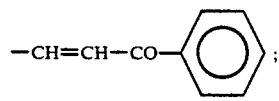

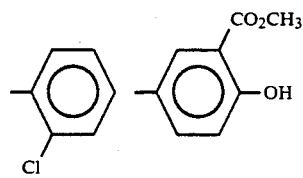

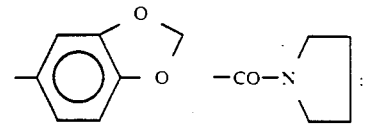

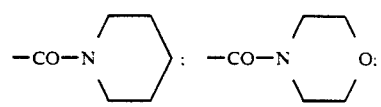

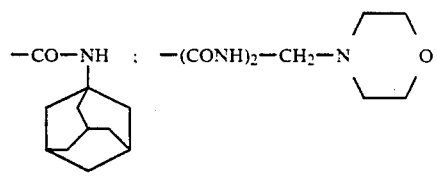

Salts and other derivatives of the compounds of Formula I-B, likewise of pharmocological interest, such as N-oxides and quaternary ammonium slats are also included within the scope of the present invention, as well as the process for the production of these compounds and their derivatives, and therapeutic applications of the same.

The compounds according to the present invention possess a marked vasodilatory activity, as will be set forth further below.

The compounds defined by the general formula I-B are prepared by reacting a piperazine of the general formula II-B

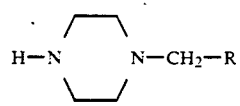

II-B wherein R is the same as in the general formula I-B, with a halogen derivative of the formula III-B

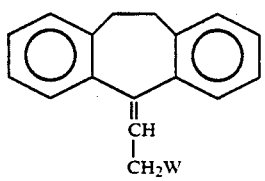

III-B wherein W is bromine or chlorine.

The reaction is carried out in an inert solvent and in the presence of a hydrogen halide binder, which may be an inorganic or organic base, or an excess of the original amine.

The compounds of the general formula I-B may also be prepared by reacting the piperazine of the formula IV-B

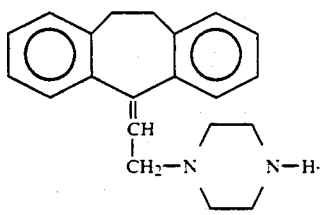

IV-B with a halogen derivative of the general formula W—CH₂—R, wherein W and R are the same as previously described.

The reaction is carried out in the same manner as before with the same conditions.

Finally, the compounds of the general formula I-B may also be prepared by reacting the aldehyde of the formula V-B:

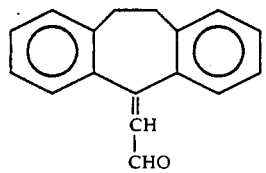

V-B with a piperazine of the general formula II-B (as before), in the presence of a reducing agent such as sodium borohydride or catalytic hydrogenation.

An alternative form for the compounds of the formula I-B includes salts thereof with minimal acids, such as, for example, hydrochloric, sulfuric or nitric acid, or with organic acids, such as, for example, oxalic, salicylic, citric, maleic or fumaric acid. The employment of hydrochloric or maleic acid is, however, preferable, due to their favorable pharmocological properties.

EXAMPLES

EXAMPLE 1

Preparation of N-benzyl-N'-2-(10,11-dihydrodibenzo-(a,d)-cyclohept-5-yliden)-ethylpiperazine A mixture of 5.10 gr (20 mmol) of 2-chloro-1-(10,11-dihydrobenzo-(a,d)-cyclohept-5-yliden)-ethane and 3.52 gr (20 mmol) of N-benzylpiperazine is refluxed in 100 ml acetonitrile for 4 hours in presence of 2.52 gr (3 mmol) of sodium bicarbonate.

The mixture is then cooled and filtered followed by elimination of the solvent and recrystallization of the residue from 10 ml of acetone. In this manner 3.78 gr of N-benzyl-N'-2-(10, 11-dihydrodibenzo(a,d)-cyclohept-5-yliden)-ethylpiperazine are obtained. Yield 48%.

Analytical data:
Melting point: 128°–130° C.
IR: 30,55,3015, 2930, 2800, 1600, 1485, 1450, 1145, 1010, 770, 755, 740 700.
NMR: 7.25/sc(13H); 6.0t(1H); 3.50/s(2H); 3.10/sc(8H); 2.50/s(4H); 2.35/sc(2H).

EXAMPLE 2

Preparation of N-2-(10,11-dihydrobenzo(a,d)-cvclohept-5-yliden)-ethyl-N,-(2-thenyl)-piperazine A mixture of 5.10 gr (20 mmol) of 2-chloro-1-(10,11-dihydrodibenzo-(a,d)-cyclohept-5-ylide n)-ethane and 3.64 gr (20 mmol) of N-2-thenylpiperazine is refluxed in 100 ml of chloroform for 6 hours in the presence of 2.52 gr (30 mmol) of sodium bicarbonate.

The mixture is cooled and filtered, and the solvent is eliminated, after which the residue is suspended in 50 ml of acetone and treated with an excess of saturated maleic acid in acetone. The precipitate is filtered and recrystallized from water.

A product of 6.24 gr of N-2-(10,11-dihydrodibenzo-(a,d)-cyclohept -5-yliden)-ethyl-N,-2(thenyl)-piperazine associated at 1:2 with maleic acid is obtained. Yield: 50%.

Analytical data:
Melting point: 202° C. (decomposition)
IR: 3070, 3010, 1690, 1625, 870, 775, 760, 745, 650.
NMR: 8.8/sa(4H); 7.6/sc(1H); 7.3/sc(10H); 6.25/s(1H); 6.05/t(1H); 2.5–4.0/sc(16H).

EXAMPLE 3

Preparation of N-benzyl-N,-2-(10,11-dihvdrodibenzo(a,d)-cycloheot-5-yliden)-ethylpiperazine A mixture of 6.08 g (20 mmol) of N-2-(10,11-dihydrodibenzo-(a,d)-cyclohept-5-yliden) -ethylpiperazine and 2.53 g (20 mmol) of benzyl chloride in 100 ml of acetonitrile is heated under reflux for 6 hours in the presence of 2.52 g (30 mmol) of sodium bicarbonate. Working-up as in example 1 yields 3.54 g of product. (Yield: 45%).

Analytical data are the same as in example 1.

EXAMPLE 4

Preparation of N-2-(10,11-dihvdrodibenzo(a,d)-cvclohept-5-yliden)-ethyl-N,-(2-thenyl)-piperazine A mixture of 4.68g(20 mmol) of (10,11-dihydrodibenzo-(a,d)-cyclohept-5-yliden)-ethanal and 3.64 g (20 mmol) of N-2-thenyl-piperazine in 100 ml of methanol is treated with 0.76 g (20 mmol) of sodium borohydride in 10 ml of methanol.

Working-up as in Example 2 yields 6.86 g of product. (yield = 55 %).

The analytical data are the same as in Example 2.

PHARMOCOLOGICAL PROPERTIES

The compounds according to the present invention were tested for vasodilatory activity. One method employs the technique of the isolated rat hind-quarters which involves antagonizing the vasoconstrictive effect of perfusion of hyperkalaemic Tyrode solution, according to the method of F. N. Fastier and F. H. Smirk(J.-Pharm.Exp.Therap. 89, 256–270(1947)), and then calculating for the products which show the greatest activity, the $ED_{30}$, that is the dose which produces a 30 % vasodilatory activity with respect to the basic vasoconstriction.

The product of the process of Examples 1 and 3 is highly vasodilatory while the product of the method of examples 2 and 4 has almost no vasodilatory effect.

The formula for the derivatives having at least some vasodilatory effect is as follows:

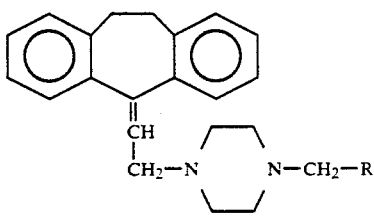

group consisting —CH=CH₂; —CO₂C₂H₅; —CH=CH—CO₂CH₃;

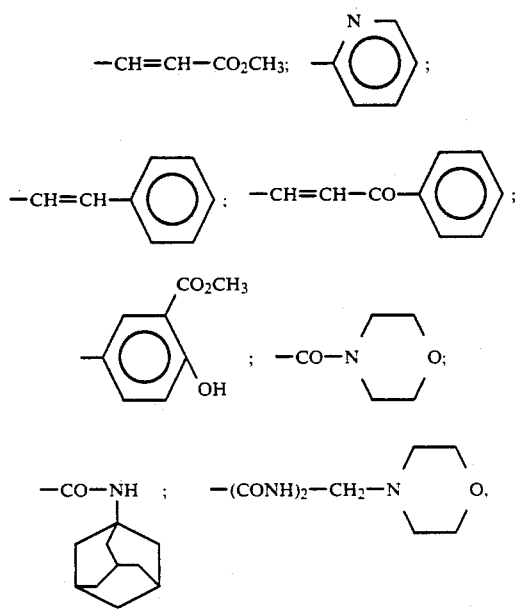

and a salt thereof

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

We claim:

1. A dihydrodibenzocycloheptylidenethylpiperazine compound having a vasodilatory effect of the formula:

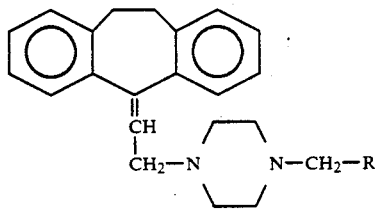

I-B wherein R represents a substituent selected from the group consisting of —CO=CH₂; —CH=CH—CO₂CH₃; —CO₂C₂H₅;

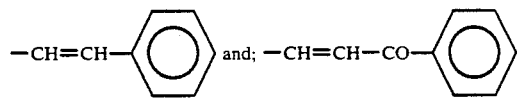

or a pharmaceutically acceptable salt thereof.

2. A dihydrodibenzocycloheptyliden-ethylpiperazine compound according to claim 1, wherein said R is —CH=CH₂.

3. The dihydrodibenzocycloheptyliden-ethylpiperazine compound according to claim 1, wherein said salt is selected from the group consisting of an N-oxide and a quaternary ammonium salt.

4. A vasodilating pharmaceutical composition containing, as an active ingredient, a therapeutically effective amount of a compound according to claim 6 and a pharmaceutical carrier.

5. A pharmaceutical composition comprising a therapeutically effective amount of a compound according to claim 1, as active ingredient, and a pharmaceutical carrier or excipient.

* * * * *